US005478554A

United States Patent [19]

Behler et al.

[11] Patent Number: 5,478,554

[45] Date of Patent: Dec. 26, 1995

[54] PROCESS FOR REDUCING THE CONTENT OF FREE FROMALDEHYDE AND FORMIC ACID IN NONIONIC AND ANIONIC SURFACTANTS

[75] Inventors: Ansgar Behler, Bottrop; Hermann Hensen; Uwe Ploog, both of Haan; Werner Seipel; Frank Clasen, both of Hilden, all of Germany

[73] Assignee: Henkel Kommanditgesellschaft auf Aktien, Duesseldorf

[21] Appl. No.: 307,729

[22] PCT Filed: Mar. 18, 1993

[86] PCT No.: PCT/EP93/00657

§ 371 Date: Sep. 23, 1994

§ 102(e) Date: Sep. 23, 1994

[87] PCT Pub. No.: WO93/19724

PCT Pub. Date: Oct. 14, 1993

[30] Foreign Application Priority Data

Mar. 27, 1992 [DE] Germany .......................... 42 10 073.9

[51] Int. Cl.$^6$ .............................. A61K 7/48; C11D 3/26; C11D 3/30; C11D 3/33

[52] U.S. Cl. ................................. 424/70.31; 252/174.21; 252/DIG. 5; 252/401; 424/70.14; 514/970

[58] Field of Search ............................. 424/70.31, 70.14, 424/401; 514/970; 252/DIG. 5, DIG. 14, 174.21, 174.22, 397, 401

[56] References Cited

U.S. PATENT DOCUMENTS

| | | | |
|---|---|---|---|
| 3,865,542 | 2/1975 | Kalopissis et al. | 8/405 |
| 5,034,159 | 7/1991 | Tesmann et al. | 252/551 |
| 5,071,960 | 12/1991 | Turowski et al. | 530/356 |
| 5,098,596 | 3/1992 | Balzer | 252/174.21 |
| 5,242,615 | 9/1993 | Urfer et al. | 252/174.17 |
| 5,252,244 | 10/1993 | Beaujean et al. | 252/120 |
| 5,286,406 | 2/1994 | Scholz et al. | 252/174.17 |
| 5,352,389 | 10/1994 | Gazzani | 252/544 |
| 5,397,497 | 3/1995 | Jakobson et al. | 252/170 |

FOREIGN PATENT DOCUMENTS

| | | |
|---|---|---|
| 0168719 | 1/1986 | European Pat. Off. . |
| 0186025 | 7/1986 | European Pat. Off. . |
| 0234261 | 9/1987 | European Pat. Off. . |
| 0865747 | 5/1941 | France . |
| 0060130 | 7/1985 | Japan . |
| 0068094 | 3/1992 | Japan . |

OTHER PUBLICATIONS

Schick M. J. 'Nonionic Surfactants' 1981, Marcel Dekker Inc., New York and Basel.

Angew. Chem. 90, 187 (1978).

Surfactant Science Series, vol. 23, Ed. M. J. Schick, Marcel Dekker Inc., 1987, New York and Basel.

*Primary Examiner*—Melvyn I. Marquis
*Assistant Examiner*—Robert H. Harrison
*Attorney, Agent, or Firm*—Ernest G. Szoke; Wayne C. Jaeschke; John Daniel Wood

[57] ABSTRACT

A process for reducing the content of free formaldehyde and formic acid in nonionic and anionic surfactants is provided. The process comprises adding an amine compound selected from the group consisting of a) alkanolamines, b) aminocarboxylic acids and c) oligopeptides to a surfactant comprised of a member selected from the group consisting of nonionic and anionic surfactants. The amine compound is preferably selected from the group consisting of a) an alkanolamine containing 2 to 15 carbon atoms, b) an aminocarboxylic acid containing 2 to 8 carbon atoms, and c) an oligopeptide with an average molecular weight of 500 to 5000. The nonionic and anionic surfactants preferably contain 1 to 100 ethylene oxide units in the form of at least one polyethylene glycol chain. The amine compound is preferably added in a quantity of 50 to 6000 ppm, based on active substance of said surfactant.

10 Claims, No Drawings

PROCESS FOR REDUCING THE CONTENT OF FREE FROMALDEHYDE AND FORMIC ACID IN NONIONIC AND ANIONIC SURFACTANTS

BACKGROUND OF THE INVENTION

1. Field of the Invention

This invention relates to a process for reducing the content of free formaldehyde and formic acid in nonionic and anionic surfactants by addition of selected amine compounds.

2. Discussion of Related Art

Nonionic and anionic surfactants are important raw materials for the production of personal hygiene preparations and cosmetic preparations such as, for example, foam baths, hair shampoos, body lotions or creams. Typical representatives of such surfactants are, for example, ethoxylated partial glycerides, fatty alcohol polyethylene glycol ethers and fatty alcohol ether sulfates.

However, nonionic and anionic surfactants containing ethylene oxide units in the form of polyethylene glycol ether chains are not indefinitely stable to oxidative degradation. Accordingly, in the event of prolonged storage, particularly under the influence of light and oxygen, the polyethylene glycol ether chain can undergo partial degradation with formation of formaldehyde or formic acid. Although both these substances are permitted preservatives for cosmetics and although the quantities formed are usually far below the legal limits, raw material manufacturers strive to produce surfactants with a high degree of purity, i.e. with a minimal content of impurities or degradation products. With this in mind, therefore, there is a continuing interest in minimizing the content of unwanted free formaldehyde and formic acid in anionic and nonionic surfactants.

It is known from a contribution by Donbrow on the stability of polyoxyethylene chains in Surfactant Science Series, Vol. 23, M. J. Schick (ed.), Marcel Dekker, Inc., New York/Basel, 1978, pages 1011 et seq. that the oxidative degradation of such chains is initiated and promoted by various factors and, depending on the mechanism, can be stopped by the addition of antioxidants, peroxide scavengers, chelating agents or UV adsorbers. In this connection, it is pointed out for example that phenols and amines react off with free radicals and can thus prevent the formation of peroxides.

The use of phenols and alkylamines for stabilizing products which come into contact with the human skin in their commercial form is out of the question for toxicological reasons alone. The odor-emission problems involved in their use and difficulties of making up also rule out these substances.

Accordingly, the problem addressed by the present invention was to provide a process for reducing the content of free formaldehyde and formic acid in nonionic and anionic surfactants which would be free from the disadvantages mentioned above.

SUMMARY OF THE INVENTION

The present invention relates to a process for the reducing the content of free formaldehyde and formic acid in nonionic and anionic surfactants, in which the products are stabilized by the addition of an amine compound selected from the group consisting of a) alkanolamines, b) aminocarboxylic acids and c) oligopeptides.

It has surprisingly been found that even the addition of small quantities of the amine compounds mentioned reduces or completely and permanently suppresses the formation of formaldehyde and formic acid. The stabilizers are toxicologically safe and easy to make up and do not have a lasting influence on the properties of the stabilized products.

Nonionic and anionic surfactants containing 1 to 100, preferably 2 to 30 and more preferably 2 to 10 ethylene oxide units in the form of at least one polyethylene glycol chain are stabilized by the process according to the invention.

DETAILED DESCRIPTION OF THE INVENTION

Nonionic surfactants in the context of the invention are adducts of ethylene oxide with compounds containing active hydrogen atoms or fatty acid esters.

Typical examples are fatty alcohol polyglycol ethers, alkylphenol polyglycol ethers, fatty acid polyglycol esters, fatty acid amide polyglycol ethers, fatty amine polyglycol ethers, alkyl glucoside polyglycol ethers, mixed ethers, ethylene oxide/propylene oxide copolymers and polysorbates and ethoxylation products of fatty acid esters, such as for example triglycerides or partial glycerides. The process has proved to be particularly effective for stabilizing fatty alcohol polyglycol ethers and ethylene oxide adducts with partial glycerides.

Anionic surfactants are understood to be adducts of ethylene oxide with compounds containing active hydrogen atoms or fatty acid esters which, in addition, contain at least one sulfate, sulfonate, carboxylate and/or phosphate group in the molecule.

Typical examples are fatty alcohol polyglycol ether sulfates, terminal and internal alkyl polyglycol ether sulfonates, polysorbate sulfates, sulfosuccinates, ethylene oxide adducts with sulfonated fatty acid esters, alkyl polyglycol ether phosphates and alkyl polyglycol ether carboxylates. The process has proved to be particularly effective for stabilizing fatty alcohol polyglycol ether sulfates.

Alkanolamines containing 2 to 15 carbon atoms may be used for stabilizing the nonionic and anionic surfactants. Typical examples are monoethanolamine, mono-n-propanolamine, mono-i-propanolamine, monobutanolamine, monopentanolamine and tetrahydroxypropyl ethylenediamine. Monoalkanolamines are preferably used, monoethanolamine being particularly preferred.

Aminocarboxylic acids containing 2 to 8 carbon atoms may be used as a further stabilizer component. Typical examples are alanine, arginine, asparagine, cysteine, cystine, dibromotyrosine, diiodotyrosine, glutamine, glutamic acid, histidine, hydroxylysine, hydroxyproline, isoleucine, leucine, lysine, methionine, phenylalanine, proline, serine, threonine, thyroxine, tryptophane, tyrosine and valine. Glycine is preferably used for stabilization.

In addition, oligopeptides of which the degree of oligomerization is sufficiently low to guarantee complete solubility in water under in-use conditions and in the in-use concentration, for example oligopeptides with an average molecular weight of 500 to 5000, are also suitable for stabilization. Water-soluble products of the type formed, for example, in the partial hydrolysis of proteins, for example gelatine or collagen [Angew Chem. 90, 187 (978)] are particularly suitable.

The stabilizers may be added to the surfactants in quantities of 50 to 6000 ppm and preferably in quantities of 500 to 5000 ppm, based on active substance of the surfactants to be stabilized.

The nonionic and anionic surfactants stabilized by the process according to the invention are substantially free from formaldehyde and formic acid formed by oxidative degradation of the polyethylene glycol chain and are suitable for the production of laundry detergents, dishwashing detergents and cleaning products and for the production of hair-care and personal hygiene products in which they may be present in quantities of 0.1 to 50% by weight and preferably 1 to 25% by weight, based on the particular product.

The following Examples are intended to illustrate the invention without limiting it in any way.

EXAMPLES

Test method. Aqueous, approximately 30% by weight surfactant pastes accommodated in closed, light glass bottles were stored for 3 months at a temperature of 20° C. in the presence of light with and without addition of a stabilizer. The formaldehyde and formic acid contents were determined by gas chromatography, the final value after storage for 3 months with no addition of a stabilizer being recorded as 100%.

Example 1

Surfactant paste:

Adduct of on average 7 moles of ethylene oxide with a commercial $C_{8/18}$ coconut oil monoglyceride (Cetiol® HE, a product of Henkel KGaA, Düsseldorf, FRG).

Stabilizer:

Monoethanolamine (MEA)

| Stabilizer | Formaldehyde (%-rel) after months | | | |
|---|---|---|---|---|
| ppm | 0 | 1 | 2 | 3 |
| 0 | <1 | 19 | 38 | 100 |
| 500 MEA | <1 | 7 | 10 | 12 |
| 5000 MEA | <1 | <1 | <1 | <1 |

Example 2

Surfactant paste:

$C_{12/14}$ coconut oil fatty alcohol 2 EO sulfate sodium salt (Texapon® N, a product of Henkel KGaA, Düsseldorf, FRG).

Stabilizers:

Monoethanolamine (MEA)

Glycine (GLY)

Collagen hydrolyzate (molecular weight approximately 2000–5000) (KH)

| Stabilizer | Formaldehyde (%-rel) after months | | | |
|---|---|---|---|---|
| ppm | 0 | 1 | 2 | 3 |
| 0 | <1 | 4 | 8 | 100 |
| 500 MEA | <1 | 4 | 16 | 21 |
| 5000 MEA | <1 | <1 | <1 | <1 |
| 500 GLY | <1 | 4 | 6 | 66 |
| 5000 GLY | <1 | <1 | <1 | <1 |

-continued

| Stabilizer | Formaldehyde (%-rel) after months | | | |
|---|---|---|---|---|
| ppm | 0 | 1 | 2 | 3 |
| 500 KH | <1 | 4 | 7 | 52 |
| 5000 KH | <1 | <1 | <1 | <1 |

Example 3

Surfactant paste:

$C_{12/14}$ coconut oil fatty alcohol 2 EO sulfate sodium salt (Texapon® N, a product of Henkel KGaA, Düsseldorf, FRG).

Stabilizer:

Monoethanolamine (MEA)

| Stabilizer | Formic acid (%-rel) after months | | | |
|---|---|---|---|---|
| ppm | 0 | 1 | 2 | 3 |
| 0 | <1 | 28 | 53 | 100 |
| 5000 MEA | <1 | <1 | <1 | <1 |

We claim:

1. A process for reducing the content of free formaldehyde and formic acid in nonionic and anionic surfactants, comprising adding an amine compound selected from the group consisting of a) alkanolamines, b) aminocarboxylic acids and c) oligopeptides to a surfactant comprised of a member selected from the group consisting of nonionic and anionic surfactants.

2. A process as claimed in claim 1 wherein said surfactant contains 1 to 100 ethylene oxide units in the form of at least one polyethylene glycol chain.

3. A process as claimed in claim 1 wherein said surfactant is selected from the group consisting of an adduct of ethylene oxide with a compound containing an active hydrogen atom and a fatty acid ester.

4. A process as claimed in claim 1 wherein said surfactant is an anionic surfactant selected from the group consisting of adducts of ethylene oxide with a compound containing an active hydrogen atom and a fatty acid ester, anionic surfactant containing at least one sulfate, sulfonate, carboxylate and/or phosphate group in the molecule.

5. A process as claimed in claim 1 wherein said amine compound is an alkanolamine containing 2 to 15 carbon atoms.

6. A process as claimed in claim 1 wherein said amine compound is an aminocarboxylic acid containing 2 to 8 carbon atoms.

7. A process as claimed in claim 1 wherein said amine compound is an oligopeptide with an average molecular weight of 500 to 5000.

8. A process as claimed in claim 1 wherein said amine compound is added in a quantity of 50 to 6000 ppm, based on active substance of said surfactant.

9. A process as claimed in claim 1 wherein the amount of said amine compound is sufficient to suppress the formation of formaldehyde and formic acid in said surfactant.

10. A process for reducing the content of free formaldehyde and formic acid in nonionic and anionic surfactants, comprising adding an amine compound selected from the group consisting of a) an alkanolamine containing 2 to 15 carbon atoms, b) an aminocarboxylic acid containing 2 to 8 carbon atoms, and c) an oligopeptide with an average molecular weight of 500 to 5000 to a surfactant comprised of a member selected from the group consisting of nonionic and anionic surfactants, said nonionic and anionic surfactants containing 1 to 100 ethylene oxide units in the form of at least one polyethylene glycol chain, wherein said amine compound is added in a quantity of 50 to 6000 ppm, based on active substance of said surfactant.

* * * * *